United States Patent [19]

Strauss

[11] 4,024,211
[45] May 17, 1977

[54] CASTING TECHNIQUE FOR PROSTHETIC DENTISTRY

[75] Inventor: Albert E. Strauss, Malibu, Calif.

[73] Assignee: A. E. Strauss Company, Incorporated, Malibu, Calif.

[22] Filed: Oct. 14, 1975

[21] Appl. No.: 621,838

[52] U.S. Cl. .............................. 264/16; 264/221; 264/317

[51] Int. Cl.² ........................................... B29C 5/00

[58] Field of Search .............................. 264/16–18, 264/219, 221, 317

[56] References Cited

UNITED STATES PATENTS

| | | | |
|---|---|---|---|
| 1,680,312 | 8/1928 | Whiteley | 264/317 |
| 2,477,268 | 7/1949 | Saffir | 264/18 |
| 2,576,206 | 11/1951 | Barth | 264/219 |
| 3,102,337 | 9/1963 | Mintz | 264/19 |
| 3,470,935 | 10/1969 | Prosen | 264/19 |

OTHER PUBLICATIONS

Knowles, Jour. of Prosthetic Dentistry, vol. 13 (1963) pp. 679–687 relied on.

Primary Examiner—Willard E. Hoag
Attorney, Agent, or Firm—Flam & Flam

[57] ABSTRACT

A female attachment for a dental prosthetic device is made by embedding the precision male part of a precision core into a wax-up, leaving the anchor part thereof exposed; sculpting the wax at the boundary line between said precision male part and said anchor part; investing the wax-up and core with investment material; removing the wax, leaving the core and the investment material to form a mold cavity; casting the prosthetic part in the mold cavity to form a female attachment in the resulting prosthetic device; and thereafter removing the core and the investment material.

3 Claims, 7 Drawing Figures

CASTING TECHNIQUE FOR PROSTHETIC DENTISTRY

FIELD OF INVENTION

This invention relates to dental prosthetic devices and more particularly to a method of casting interlocking female attachments and companion parts. The invention is particularly useful with dowel attachments of the type suggested by Dr. Alex Thompson and as more fully explained by L. E. Knowles, D.D.S., in an article entitled DOWEL ATTACHMENT REMOVABLE PARTIAL DENTURE as published in the *Journal of Prosthetic Dentistry*, 13:679–687, 1963.

It has become increasingly common to utilize dowel attachments for partial dentures that are either removably or permanently attached. Typically, a rooted tooth component is made to provide an upwardly opening tapered dowel recess to receive a companion tapered dowel protuberance of the adjoining bridge section. In order to cast these recesses and protuberances by the lost wax method, it has been common for dental supply houses to make available plastic inserts for inclusion in the wax pattern. If a female dowel part, for example, is to result in the cast gold or other material, the wax pattern will be made to incorporate a plastic female part that corresponds to the finished work. In a well known manner, the pattern produces a mold cavity in investment material cast about the pattern. The wax and plastic are burned away, leaving the mold cavity.

In order to make a perfect casting of the dowel recess, the investment material must completely and accurately fill the recess in the plastic component of the attachment set. If air is trapped, an incomplete fill will result. Later touchup of the finished work will be required and some accuracy will be lost.

The problem has been recognized. Very great care has been used by painting the investment material into the cavity of the plastic part preparatory to full investment. The wax pattern can be vibrated after it has been newly painted in order to cause air bubbles to surface. This is not always successful.

Investing about the male component of the set is far easier. There are no pockets for entrappment of air. A good component results.

The primary object of this invention is to provide accurate casting of the female component of an attachment set.

SUMMARY OF THE INVENTION

In order to achieve the foregoing object, I provide a precision core. The core has two parts. One part is a precision negative of the recess to be formed in the work. The second part is an anchor to be surrounded by the investment material. The core remains when the wax is burned out. Since it is a precision production part, it avoids the requirement of investing a small recess. The core has characteristics corresponding to those of the investment materials so that it is removed from the finished work therewith, either by leaching, blasting or the like. A perfect female attachment component is accordingly provided.

BRIEF DESCRIPTION OF THE DRAWINGS

A detailed description of the invention will be made with reference to the accompanying drawings wherein like numerals designate corresponding parts in the several figures.

DETAILED DESCRIPTION OF PREFERRED EMBODIMENT

The following detailed description is of the best presently contemplated mode of carrying out the invention. This description is not to be taken in a limiting sense, but is made merely for purposes of illustrating the general principles of the invention since the scope of the invention is best defined by the appended claims.

Figure 1:
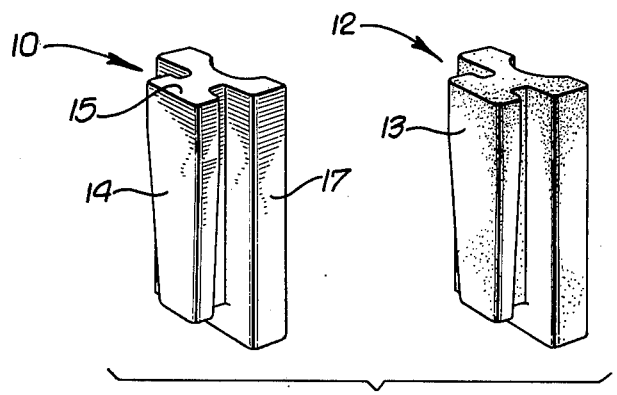
FIG. 1 is a perspective view of a set of casting components (both male) for use in practicing the present invention.
Figure 2:
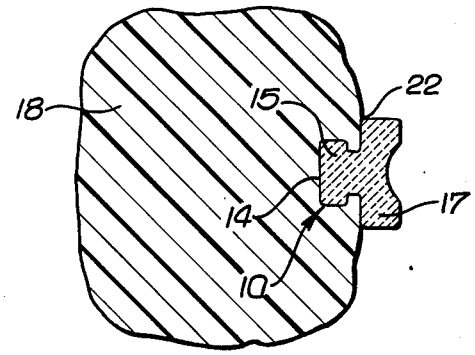
FIG. 2 is a diagrammatic view illustrating the wax pattern and core attached together ready for investment.
Figure 3:
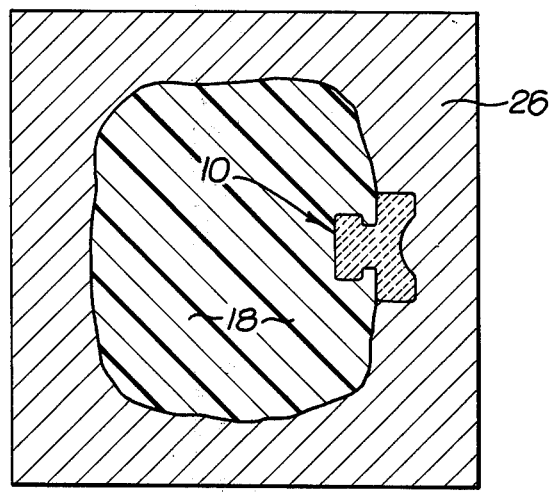
FIG. 3 is a diagrammatic view showing the invested parts.
Figure 4:
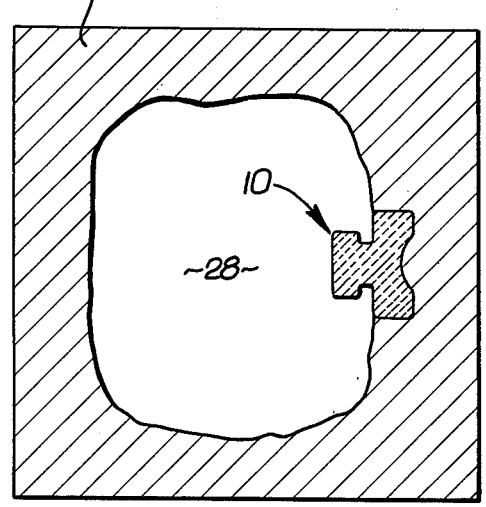
FIG. 4 is a diagrammatic view of the mold ready for casting, the wax having been burned out.

In FIG. 1 there is shown a set of attachment devices comprising components 10 and 12. The components 10 and 12 are similar in that both have male configurations. However, the component 10 is a core made of material that will not burn out with the wax whereas the component 12 is made of material that will. The manner in which the components are used in the casting process is diagrammatically illustrated in FIGS. 2 to 7.

The components have precision attachment surfaces 13 and 14. The manner in which the core component 10 is used will now be described. The core 10 has two parts, a precision male or negative 15 that provides the surface 14 and an anchor part 17. The entire precision surface 14 of the core 10 (FIG. 2) is worked into the wax pattern (wax-up) 18 so that the anchor portion 17 of the component 10 is exposed along the carefully sculpted boundary line 22. The wax pattern and the component 10 are then invested, that is, encased in investment material 26 (FIG. 3) which conforms precisely to the wax and core 10 as the material hardens. The wax is then burned out and the cavity 28 (FIG. 4) remains with the core component 10 in place. The casting is then made of gold or other suitable material.

The investment material 26 and the core 10 are thereafter removed. The removal may be accomplished by leaching in a molten caustic soda solution at an elevated temperature or by etching with hydrafluoric acid at room temperature. Optionally the investment material may be blasted away in which case the core component 10 is made of selectively destructible ceramic materials. In any case, the component is inert, stable in high temperatures, casting environments and shock resistant. Mixes of oxides of silicon, aluminum, magnesium, etc. suitable for the present application are known in the ceramic arts and may be supplied, for example, by Coors Porcelain of Golden, Colo.

Figure 5:
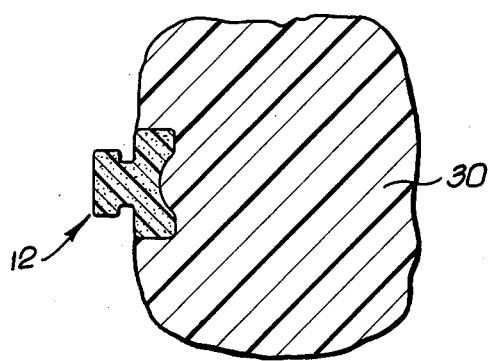
FIG. 5 is a view similar to FIG. 2 but showing the plastic companion component embedded in the wax material with precision surfaces exposed.
Figure 6:
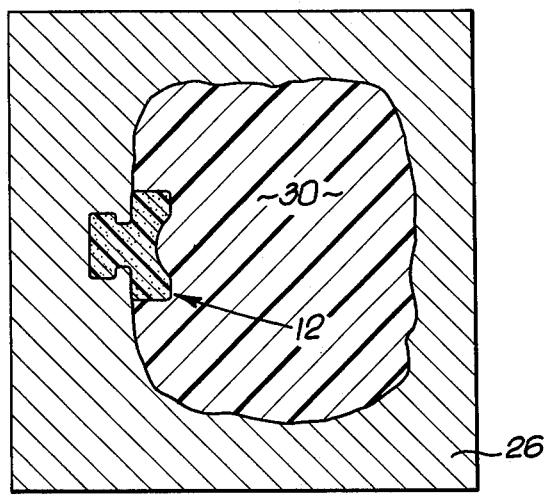
FIG. 6 is a view similar to FIG. 3 showing the invested parts.
Figure 7:
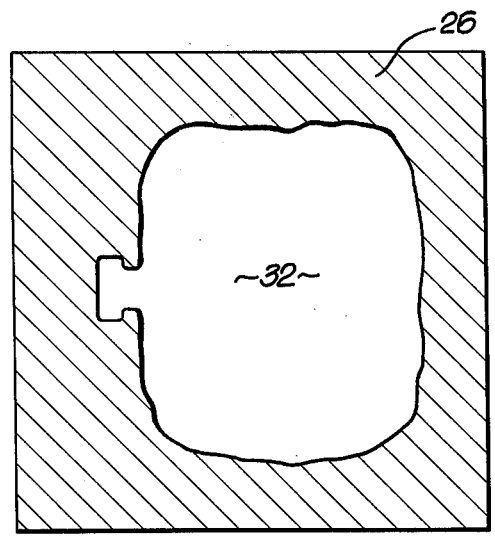
FIG. 7 is a view of the resulting cavity.

In order to make the companion male part, the companion mold component 12 as shown in FIG. 5 is embedded in the wax 30. The components 12 and 30 are then invested as indicated in FIG. 6. The components 12 and 30 are together burned away, leaving the cavity 32 shown in FIG. 7. The resulting casting provides a male component that will fit the recess of the casting made by the molding recess 28 shown in FIG. 4. Of course the components 10 and 12 are precisely made to achieve an exact fit of the resulting parts.

Intending to claim all novel, useful and unobvious features shown or described, I make the following claims:

1. The process of making a female attachment for a dental prosthetic device by the aid of a precision core having an anchor part and an adjoining precision male part corresponding to the female attachment to be made, and by the aid of a thermoplastic "wax" and investment material, said process comprising:
   a. making a wax-up or pattern composite of wax and said core including the steps of embedding said precision male part of said core in said "wax", exposing said anchor part and sculpting the "wax" at the boundary line between said parts of said core;
   b. investing the pattern with investment material including the step of surrounding said anchor part therein;
   c. removing the wax by heating, leaving the core and the investment material to form a mold cavity;
   d. casting a molding material in the mold cavity to form a prosthetic device having a female attachment; and
   e. thereafter removing the core and the investment material by the same process, the core and the investment material having a similar degradable characteristic and materials of both said core and said investment being unaffected by said heating.

2. The process of making a set of companion dowel attachments for a dental prosthetic device by the aid of a (1) core having an anchor part and an adjoining precision male part corresponding to the female dowel attachment; (2) a plastic male part having a precision part corresponding to the male dowel attachment; and (3) thermoplastic wax and investment material; said process comprising:
   a. making a wax-up or pattern composite of wax and said core including the steps of embedding said precision male part of said core in said wax, exposing said anchor part and sculpting the wax at the boundary line between said parts of said core;
   b. investing the pattern with investment material including the step of surrounding said anchor part therein;
   c. removing the wax, leaving the core and the investment material to form a mold cavity;
   d. casting the prosthetic part in the mold cavity to form a female attachment in the resulting prosthetic device;
   e. thereafter removing the core and the investment material;
   f. making a second wax-up or pattern composite of wax and said plastic male part, including the steps of partially embedding said plastic male part while exposing the precision part thereof and sculpting the wax at the boundary of said precision part of said plastic male part;
   g. investing the second pattern with investment material, including the step of surrounding said precision male part of said plastic male part with investment material;
   h. removing the second pattern from its investment material to form a second mold cavity;
   i. casting the companion prosthetic part in said second mold cavity to form a male attachment; and
   j. thereafter removing the investment material from the cast companion prosthetic part.

3. The process as set forth in claim 2 in which the removal of the core and the investment material is performed by the same process, the core and the investment material having a similar degradable characteristic; the removal of the second pattern being performed in one operation the wax and the plastic male part having a similar degradable characteristic.

* * * * *